US007618648B2

(12) United States Patent
Gerhardt et al.

(10) Patent No.: US 7,618,648 B2
(45) Date of Patent: *Nov. 17, 2009

(54) SATIETY INDUCING COMPOSITION

(75) Inventors: Cinderella Christina Gerhardt, Vlaardingen (NL); Maria Catherine Tasker, Vlaardingen (NL)

(73) Assignee: UNILEVER Bestfoods, North America division of Conopco, Inc., Englewood Cliffs, NJ (US)

( * ) Notice: Subject to any disclaimer, the term of this patent is extended or adjusted under 35 U.S.C. 154(b) by 116 days.

This patent is subject to a terminal disclaimer.

(21) Appl. No.: 10/519,657

(22) PCT Filed: Jun. 13, 2003

(86) PCT No.: PCT/EP03/06212

§ 371 (c)(1),
(2), (4) Date: Dec. 22, 2004

(87) PCT Pub. No.: WO2004/002241

PCT Pub. Date: Jan. 8, 2004

(65) Prior Publication Data

US 2005/0238694 A1 Oct. 27, 2005

(30) Foreign Application Priority Data

Jul. 1, 2002 (EP) .................................. 02254622

(51) Int. Cl.
A23C 21/02 (2006.01)
A61K 38/01 (2006.01)
(52) U.S. Cl. ........................ 424/439; 426/583; 426/648; 514/21; 530/343
(58) Field of Classification Search .................. None
See application file for complete search history.

(56) References Cited

U.S. PATENT DOCUMENTS

| 5,039,532 | A | 8/1991 | Jost et al. | |
|---|---|---|---|---|
| 5,254,351 | A | 10/1993 | De Boer et al. | |
| 5,821,217 | A | 10/1998 | Forse et al. | 514/2 |
| 6,207,638 | B1 | 3/2001 | Portman | |
| 6,630,320 | B1* | 10/2003 | Davis et al. | 435/24 |
| 2002/0019334 | A1 | 2/2002 | Portman | 514/2 |
| 2002/0037830 | A1 | 3/2002 | Berthelsen et al. | 514/2 |
| 2002/0044988 | A1 | 4/2002 | Fuchs et al. | |
| 2002/0061359 | A1* | 5/2002 | Baker et al. | 426/583 |
| 2002/0081315 | A1* | 6/2002 | Katz et al. | 424/195.16 |
| 2003/0004095 | A1 | 1/2003 | Reimer et al. | |
| 2003/0165574 | A1* | 9/2003 | Ward et al. | 424/535 |
| 2004/0248768 | A1* | 12/2004 | Garcia-Rodenas et al. | 514/2 |
| 2005/0238694 | A1 | 10/2005 | Gerhardt et al. | 424/439 |
| 2006/0105938 | A1 | 5/2006 | Siemensma et al. | |
| 2006/0159770 | A1 | 7/2006 | Garcia-Rodenas et al. | |
| 2006/0171992 | A1 | 8/2006 | Gerhardt et al. | |

FOREIGN PATENT DOCUMENTS

| CA | 2 489 942 | | 1/2004 |
|---|---|---|---|
| EP | 629 350 | | 12/1994 |
| EP | 1 034 704 | A | 9/2000 |
| EP | 1 112 693 | | 7/2001 |
| EP | 1 201 137 | A | 5/2002 |
| WO | WO 93/04593 | * | 3/1993 |
| WO | 98/02165 | | 1/1998 |
| WO | 99/49741 | A | 10/1999 |
| WO | 01/37850 | | 5/2001 |
| WO | WO 01/37850 | | 5/2001 |
| WO | 01/43563 | A | 6/2001 |
| WO | 01/85984 | | 11/2001 |
| WO | 02/15719 | | 2/2002 |
| WO | 2004/002241 | | 1/2004 |
| WO | WO 2004/024177 | | 3/2004 |
| WO | WO 2004/049833 | A1 | 6/2004 |
| WO | WO 2004/049834 | A1 | 6/2004 |
| WO | WO 2004/056207 | A1 | 7/2004 |
| WO | WO 2004/069265 | A1 * | 8/2004 |
| WO | WO 2005/000325 | | 1/2005 |
| WO | WO 2007/116091 | A1 | 10/2007 |

OTHER PUBLICATIONS http://www.wheyprotein.com/sec6.html.*
Aoyama et al. Effect of Soy and Milk Whey Protein Isolates . . . Bioscience Biotechnology and Biochemistry. 2000, vol. 64, No. 12, pp. 2594-2600.*
Hall et al. Investigation into the effects of casein and whey protein . . . Proceedings of the Nutrition Society. 2001, vol. 60, p. 227A.*
Kelly et al. Innovative Dairy Ingredients. The World of Food Ingredients. Oct./Nov. 2002, pp. 24-26, 28, 30, and 32.*
Biozate 1. Nutraceuticals World. Nov. 2002 (printed Mar. 24, 2009).*
Pins et al. The Antihypertensive Effects Of A Hydrolyzed Whey Protein Supplement. Cardiovascular Drugs and Therapy. May 2002, vol. 16, Supplement 1, p. 68, Abstract P370.*
PCT International Search Report on International Application No. PCT/EP 03/06212 dated Nov. 4, 2003.
Stolk et al., "Gallbladder Motility and Cholecystokinin Release during Long-Term Enteral Nutrition in Patients with Crohn's Disease", Scan J Gastroenterol, 1994, 29: 934-939.
Nishi et al., "Dietary Protein Peptic Hydrolysates Stimulate Cholecystokinin Release Via Direct Sensing by Rat Intestinal Mucosal Cells", 2001, Exp. Biol. Med, 226:1031-1036.
Deming et al., "Effect of a Hypocaloric Diet, Increased Protein Intake and Resistance Training on Lean Mass Gains and Fat Mass Loss in Overweight Police Officers", 2000, Ann. Nutr. Metab., 44:21-29.

(Continued)

Primary Examiner—Jeffrey E Russel
(74) Attorney, Agent, or Firm—Rimma Mitelman

(57) ABSTRACT

The invention provides the use of a whey protein and/or whey protein hydrolysate which stimulate the cellular release of the satiety peptides choleocystokinin and glucagon-like-peptide in the preparation of edible compositions. The edible compositions can be used to control body weight and have beneficial effects on satiety. Edible compositions are also provided.

7 Claims, 1 Drawing Sheet

OTHER PUBLICATIONS

Communication of a Notice of Opposition dated Nov. 23, 2007, Application No. 03761459.1-1221/1517619.

Drucker, "*Development of Glucagon-Like Peptide-1-Based Pharmaceuticals as Therapeutic Agents for the Treatment of Diabetes*", Current Pharmaceutical Design, 2001, 7, pp. 1399-1412.

Zander et al., "*Effect of 6-week course of glucagon-like peptide 1 on glycaemic control, insulin sensitivity, and β-cell function in type 2 diabetes: a parallel-group study*", the Lancet, vol. 359, Mar. 9, 2002, pp. 824-830.

Toft-Nielsen, "*Determinants of the effectiveness of glucagon-like peptide-1 in type 2 diabetes*" J. Clinical Endocrinol Metab 2001, 8/86(8): 3853-60.

Sensi et al., "*Chronobiological Aspects of Weight Loss in Obesity: Effects of Different Meal Timing Regimens*", Chronobiology International, vol. 4, No. 2, 1987, pp. 251-261.

Harper, "*Biological Properties of Whey Components A Review*", The American Dairy Products Institute, 2001, pp. 1-20.

Harper, "*Biological Properties of Whey Components A Review*", The American Dairy Products Institute, 2004, pp. 1-44.

Nuttal et al., "*Effect of Protein Ingestion on the Glucose and Insulin Response to a Standarized Oral Glucose Load*", Diabetes Care, vol. 7, No. 5, Sep.-Oct. 1984, pp. 465-470.

Abubakar et al. "*Structural Analysis of New Antihypertensive Peptides Derived from Cheese Whey Protein by Proteinase K Digestion*", J. Dairy Science, vol. 81, No. 12, 1998, pp. 3131-3138.

Co-pending Application: Applicant: Gerhardt et al., U.S. Appl. No. 10/539,434, filed Jan. 13, 2006.

Information taken from the Mintel Global New Products Database Record #10089034 (www.gnpd.com) for Designer Whey Protein Blast Supplement Drink, "date published" Jul. 24, 2001.

Information taken from the Mintel Global New Products Database Record #10089034 (www.gnpd.com) for Mintel, Designer Whey Protein Blast Supplement Drink, "date published" Feb. 22, 2002.

Information taken from Internet (www.designerwhey.com) on May 2008 regarding Designer Whey citing the History of Whey.

Information taken from the Internet (www.designerwhey.com) May 2008 on Designer Whey Protein and various products.

Press release from Davisco Foods International re award for its Patented Hypertension-Reducing Whey Protein, taken from the Internet on May 2008 (www.designerwhey.com) dated May 28, 1999.

Press Release, "Antihypertensive Effects of Whey Protein Hydrolysates in Rats Reduces Mean Arterial Blood Pressure," dated Jun. 12, 2000 taken from Davisco Foods International website on May 2008.

Information from the Internet on Designer Whey, Science at Work, Davisco Foods International, accessed May 9, 2008.

Information taken from the Internet (www.designerwhey.com) on Research & Innovation of whey protein, Davisco Foods International, accessed May 9, 2008.

Patent Abstracts of Japan Publication No. 2004051623 A, Feb. 19, 2004.

"*Whey Protein Hydrolysate*", Nutraceuticals NOW, Summer 2001.

Houston, "*The Role of Vascular Biology, Nutrition, and Nutraceuticals in the Prevention and Treatment of Hypertension*", Journal of the American Nutraceutical Association, Supplement No. 1, Apr. 2002, pp. 1-71.

Langley-Danysz, "*Les peptides bio-actifs du lait deviennent une réalité*", Techno Solutions, May 2002, p. 66-67 (with English abstract).

\* cited by examiner

SATIETY INDUCING COMPOSITION

FIELD OF THE INVENTION

The present invention relates to the use of certain whey proteins and whey protein hydrolysates in the preparation of an edible composition for enhancing satiety in humans or animals. It also relates to a method of controlling body weight using these whey proteins and whey protein hydrolysates and to an edible composition comprising them.

BACKGROUND OF THE INVENTION

The incidence of obesity and the number of people considered overweight in countries where a so-called Western diet is adopted has increased over the last decade. Since obesity and being overweight are associated with a variety of diseases such as heart disease, hypertension and arthereosclerosis, this increase is a major health concern. Furthermore, being overweight is considered by the majority of the Western population as unattractive.

This has led to an increasing interest by consumers in their health and has created a demand for products which help to reduce or control daily caloric intake and/or control body weight and/or bodily appearance. Preferably, such products can be added to ordinary foodstuffs, or they can be consumed prior to, during, after or instead of an ordinary meal. Consuming such a composition should, ideally, increase and/or prolong the feeling of satiety for the consumer and/or extend the time interval between meals and/or reduce the amount of calories consumed in a subsequent meal.

Recognising the demand for efficient and convenient satiety-inducing products, research has been carried out to find compounds that stimulate the release of certain peptides associated with signaling, or causing, the feeling of satiety. These peptides are referred herein as "satiety peptides". Such satiety peptides include, for example, cholecystokinin (CCK), enterostatin, somatostatin, amylin and glucagon-like-peptides (GLP), such as glucagon-like-peptide-1 (GLP-1).

Although a great number of molecules or compositions have been suggested to be active in stimulating the release of one of the aforementioned satiety peptides, only very few of them have been derived from natural products and/or can be used in food products.

U.S. Pat. No. 6,207,638 discloses a nutritional composition stimulating the release of CCK, the composition comprising a) a protein selected from casein, whey and soy, b) a glycomacropeptide, c) a long chain fatty acid, and d) soluble and insoluble fibers. Whey protein hydrolysates are not disclosed and no teaching is given of the release of both CCK and glucagon-like-peptides by the whey protein.

WO 01/37850 discloses a milk protein hydrolysate inducing the release of glucagon-like-peptide 1 (GLP-1). Caseinoglycomacropeptide has not been found to stimulate the cellular release of CCK.

WO 02/15719 discloses nutritional compositions comprising hydrolysed whey proteins to provide reduced satiety effects from the compositions. The nutritional compositions are intended for people suffering from reduced appetite such as those convalescing and anorexia suffers.

WO 99/49741 discloses a method for providing glutamine to a patient in need thereof. The glutamine may be provided by a whey protein or a whey protein hydrolysate. Hydrolysed sweet whey may be used but no further details are given of suitable types.

US 2002/0044988 discloses compositions and methods that stimulate body protein synthesis to improve muscle mass maintenance and recovery. Whey protein hydrolysates may be used in the compositions.

EP-A-1 201 137 discloses a method of preparation of cysteine/glycine rich peptides. Hydrolysed whey protein isolates are disclosed.

EP-A-1 034 704 discloses enteral nutritional compositions that may comprise hydrolysates of milk proteins.

WO 01/43563 discloses milk protein hydrolysates for use in compositions to be used to reduce the epidemiologically established risk of diabetes mellitus type I.

Whey based energy drinks are also known in the art. Designer Whey Protein Blast drinks (ex Next Proteins, California, USA) comprises β-lactoglobulin and α-lactalbumin and are used as food supplements for building muscle mass. The drinks comprise very low levels of carbohydrates and no fat and thus the calories are provided predominantly from the protein. A bottle of 20 American ounces (about 600 ml) of the drink comprises no fat, 1 g carbohydrate and 17 g protein. The drinks are expressly instructed not to be used for weight reduction.

Powders to produce drinks comprising β-lactoglobulin and α-lactalbumin, and such drinks, are known for blood pressure lowering applications. A powder produced by Davisco Foods International (Minnesota, USA) comprises 20 g of β-lactoglobulin and α-lactalbumin, 1 g of fat and 6 g of carbohydrate per 30 g of powdered product. The powders can be mixed with water or milk to produce the drink. No disclosure is made of use in satiety control applications. The powders and drinks provide over 55% of the total calories in the powder or drink (when made with water or cow's milk) from the protein content.

However, despite the above developments, there is still a need in the art for edible compositions which provide a good satiety effect for consumers, especially those wishing to control their calorie intake and/or body weight. Furthermore, there is a need to provide such products which help with the adherence to a dietary programme, especially a calorie controlled diet or with otherwise controlling calorie intake. There is also a need for edible compositions which can be used to help improve or control perception of body image or body weight.

In particular, there is a need for edible compositions which provide an improved satiety effect compared to conventional food products or conventional diet/meal replacement products. There is also a need to provide edible compositions which have an acceptable taste as well as providing good satiety effects, e.g. the products are not too sweet, nor, too bitter.

In particular, there is a need for meal replacement products which provide one or more of the above effects and/or advantages.

The present invention seeks to address one or more of the above-mentioned problems.

In particular, it is an object of the invention to provide edible compositions which have a good satiety effect.

It is also an object of the invention to provide edible compositions which have an improved satiety effect compared to conventional food products or to conventional diet/meal replacement products.

It is also an object of the invention to provide a method to help the consumer to comply with a dietary plan, to control body weight and/or to improve or maintain the perception of body image.

SUMMARY OF THE INVENTION

Surprisingly, it has now been found that certain whey proteins (WP) and/or whey protein hydrolysates (WPH) provide an improved satiety effect. Without wishing to be bound by theory, it is believed that this occurs because they stimulate the cellular release of more than one satiety peptide.

It has been found that WP and WPH that stimulate the cellular release of both satiety peptides cholecystokinin (CCK) and glucagon-like-peptides (GLP), especially glucagon-like-peptide-1 (GLP-1) are particularly effective in inducing satiety. Such WP and WPH increase the satiety effects experienced by a person after eating an edible composition comprising them. It is believed that the combined release (either simultaneously or stepwise) of these two satiety peptides results in an enhanced feeling of satiety.

An enhanced feeling of satiety as referred to herein means a more pronounced and/or quicker feeling of satiety (satiation) and/or a longer lasting feeling of satiety after eating (satiety). Such effects typically extend the time elapsed between meals and can result in a smaller amount of food and/or number of calories being consumed daily etc. The references herein to satiety include both what is strictly referred to as "satiation" and "satiety", including "end-of-meal" satiety and "between-meals" satiety.

It is believed that the cellular release of CCK in the body is associated with the feeling of satiety that occurs at the end of a meal (end-of-meal satiety) whereas the cellular release of GLP is associated with the feeling of satiety that lasts after eating (between-meals satiety). Thus, CCK release is believed to be involved in signaling to the body when a person has eaten enough of a meal and GLP is believed to be involved in signaling to the body that we are still satiated from a previous meal.

It has also been found that the WP and WPH of the present invention exhibit an increased level of induced cellular GLP release at a given concentration than do other milk proteins, milk protein hydrolysates or non-hydrolysated whey proteins.

According to a first aspect, the present invention provides the use of a whey protein and/or whey protein hydrolysate in an edible composition, the whey protein and/or whey protein hydrolysate being able to induce the cellular release of glucagon-like-peptides and cholecystokinins, wherein the whey protein and/or whey protein hydrolysate on or after consumption of the edible composition induces an enhanced feeling of satiety.

The term "an enhanced feeling of satiety" as used herein refers to the feeling of satiety obtained upon consumption of the edible compositions of the invention compared to the feeling of satiety obtained after the consumption of an edible composition which is of substantially equivalent caloric and macro-nutrient content but wherein the whey protein and/or whey protein hydrolysate is replaced by the equivalent amount of cow's milk protein.

The edible compositions of the present invention are intended for consumption by a human or animal.

According to a second aspect, the present invention provides the use of a whey protein and/or whey protein hydrolysate in an edible composition, the whey protein and/or whey protein hydrolysate being able to induce the cellular release of glucagon-like-peptides and cholecystokinins and wherein the composition is used to improve or control perception of body image, and/or to control body weight, and/or to control calorie intake and/or help adherence to a dietary plan.

According to a third aspect, the present invention provides a method for inducing satiety in a human or animal, the method comprising the step of administering to a human or animal by means of an edible composition, an effective amount of a whey protein and/or whey protein hydrolysate which is capable of inducing the cellular release of glucagon-like peptides and cholecystokinins.

According to a fourth aspect, the present invention provides a method for improving or controlling perception of body image, and/or controlling body weight, and/or controlling calorie intake and/or helping adherence to a dietary plan, the method comprising the step of administering to a human or animal by means of an edible composition, an effective amount of a whey protein and/or whey protein hydrolysate which is capable of inducing the cellular release of glucagon-like peptides and cholecystokinins.

According to a further aspect, the present invention provides a liquid or flowable edible composition comprising protein, wherein the protein comprises 0.1 to 50% by weight based on the weight of the composition of a whey protein hydrolysate capable of inducing the cellular release glucagon-like-peptides and cholecystokinins, and wherein 50% or less of the total calories in the edible composition are provided by the protein.

A "flowable" product as referred to herein is a liquid, semi-liquid, powdered or particulate product which when poured with or without the application of pressure flows out of a container even if the product does not flow out in a continuous stream. The term does not include products which are in one piece (e.g. have a shaped solid form such as blocks, cubes etc) as these are not capable of flowing, nor, products which are eaten in a physical state which does not flow such as ice-cream.

The liquid or flowable edible compositions of the invention give good satiety effects, acceptable sensory properties (such as acceptable taste) and have a good balance of the level of whey protein and/or whey protein hydrolysate used and the percentage of calories in the product obtained from the total amount of protein in the composition. This combination is especially suitable for a meal replacement product.

According to a further aspect, the present invention provides a liquid or flowable edible composition 0.1 to 80% by weight based on the weight of the composition of a whey protein hydrolysate capable of inducing the cellular release glucagon-like-peptides and cholecystokinins, and wherein the composition further comprises added vitamins and/or minerals selected from at least one of vitamins A, B1, B2, B3, B5, B6, B11, B12, biotin, C, D, E, H, and K and calcium, magnesium, potassium, zinc and iron.

According to a further aspect, the present invention provides an edible composition in the form of a bar and comprising a total amount of from 0.1 to 80% by weight based on the weight of the composition of hydrolysates of β-lactoglobulin, α-lactalbumin or a mixture thereof.

In all of the above aspects of the invention whey protein hydrolysates are preferred. The preferred whey protein hydrolysates comprise hydrolysates of β-lactoglobulin, α-lactalbumin or a mixture thereof.

The use of the WP and/or WPH which induce the cellular release of both CCK and GLP in the preparation of edible compositions is advantageous in terms of the satiety effect obtained from the consumption of that product, compared to the use of ingredients which only induce the release of either CCK or GLP.

The advantages of the present invention include greater efficacy of the satiety effect; for example an enhanced feeling of satiety, feeling satiated sooner whilst eating and/or remaining satiated for a longer period of time after eating. These advantages are especially beneficial for the compliance with dietary plans or programmes and/or the control or maintenance of body weight and/or body perception. There are also longer term advantages associated with helping in the prevention of diseases related to being overweight.

Except in the operating and comparative examples, or where otherwise explicitly indicated, all numbers in this description indicating amounts of material or conditions of reaction, physical properties of materials and/or use are to be understood as modified by the word "about". All amounts are as percentages by weight unless otherwise stated. For the edible compositions, all percentages are by weight based on the total weight of the composition unless otherwise stated.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Figure 1:
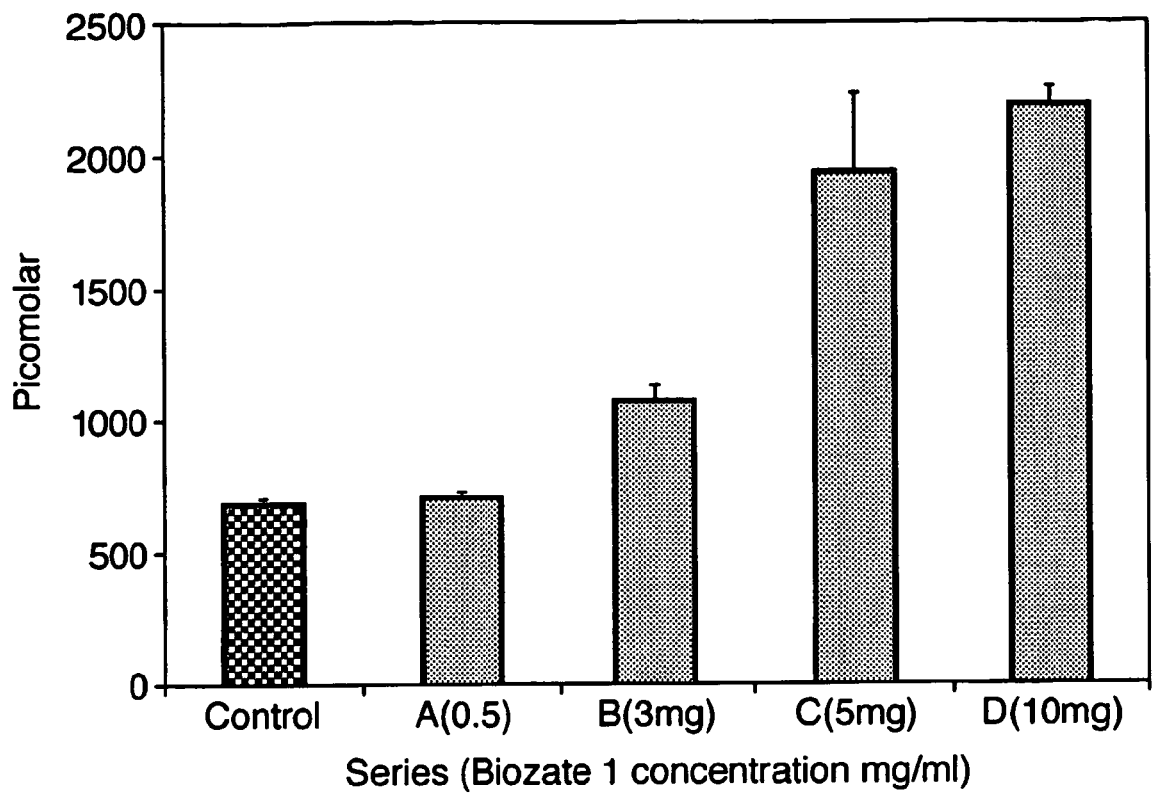
FIG. 1 shows the concentration of GLP-1 secreted from GLUTaq cells into the media after 2 hours incubation at 37° C. with the Biozate 1.
Figure 2:
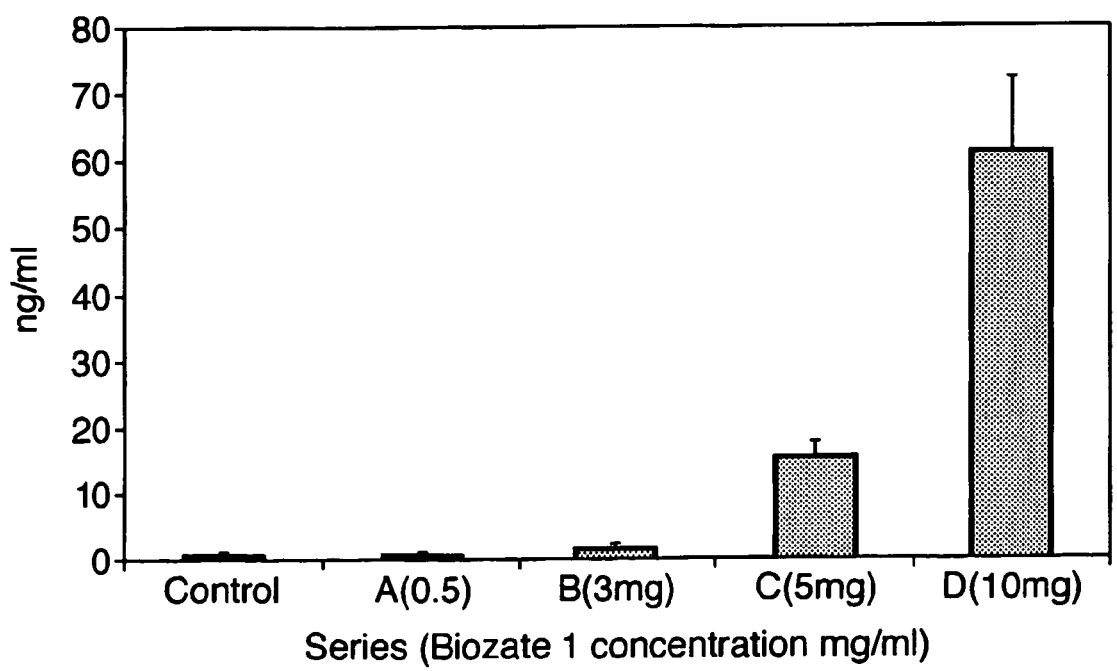
FIG. 2 shows the concentration of CCK secreted from GLUTaq cells into the media after 1 hour incubation at 37° C. with Biozate 1.

On both FIG. 1 and 2, the x axis shows the series and the concentration of Biozate 1 used. The y axes of FIG. 1 and 2 show the concentration of GLP-1 or CCK secreted from GLUTaq cells into the media after incubation. For FIG. 1 the concentration is expressed in pico moles per liter ($10^{-12}$M) and for FIG. 2 in nanograms/ml.

DETAILED DESCRIPTION

Satiety Peptides

Cholecystokinin(s) and "CCK" as used herein include all peptides of the CCK family, including (but not limited to); CCK-4, CCK-8, CCK-22, CCK-23, CCK-24, CCH-25, CCK-36, CCK-27, CCK-28, CCK-29, CCK-30, CCK-31, CCK-32, CCK-33, CCK-39, CCK-58.

Glucagon-like-peptides (GLP) and "GLP" as used herein include all peptides of the GLP family including (but not limited to); GLP-1 and GLP-2. GLP-1 has been found to be especially of interest.

Additional satiety peptides may be cellularly released by using the WP and/or WPH according to the invention. Examples of such satiety peptides include amylin, GRP-NMB, enterostatin, ApoA-IV, glucagon, somastatin, PYY, leptin and a variety of cytokines such as CNTF.

Cellular Release

Inducing the cellular release of the satiety peptides as described herein refers to inducing the release thereof by suitable cells, preferably gastrointestinal cells, after the ingestion of the whey protein (WP) and/or whey protein hydrolysate (WPH) by those cells.

Inducing the cellular release of the satiety peptides according to the invention can be measured in vitro, for example by the use of an intestinal cell line. Suitable cell lines are well known in the art. The cells used in the examples are GLUTag cells which are an L cell line from intestinal endocrine tumors arising in the large bowel in proglucagon-simian virus 40 large T antigen transgenic mice. These cells are commercially available and are further described in the publication by Drucker D. J. et al (1994): Activation of proglucagon gene transcription by protein kinase A in a novel mouse enteroendocrine cell line. *Mol Endocrinol* 8:1646-1655.

Examples 1 and 2 further illustrate the in vitro cellular release of CCK and GLP-1. The information in these examples is incorporated by reference into this section.

Without wishing to be bound by theory, it is believed that when a subject (animal or human) ingests the claimed WP and/or WPH, either by itself or as part of an edible composition, the cellular release of CCK and GLP in the body is stimulated resulting in the satiety effect.

This cellular release can also be measured in vivo, for example, by measuring the increase or appearance of CCK and GLP levels in the blood of that subject after consumption of the WP and/or WPH or an edible composition comprising it. Suitable techniques for measuring the CCK and GLP levels in the blood are well known in the art and do not need to be further described here.

The WP and/or WPH of the invention show cellular release of CCK and GLP-1 in the in vitro cellular release test of examples 1 and 2, particularly, when used at a concentration of at least 5 mg/ml.

Without wishing to be bound by theory, it is believed that the WP/WPH of the invention may provide enhanced satiety effects by at least one of the following mechanisms:

1) by triggering the release of CCK from the duodenal and jejunum mucosal (I) cells and by triggering the release of GLP-1 from mucosal L cells in the distal ileum and colon from processing of major proglucagon fragment by prohormone convertase PCI/3.
2) CCK-like peptides in the WP/WPH may activate CCK-A receptors on the gastric pylorus causing contraction resulting in gastric distension. Stomach distension activates receptors on the afferent gastric vagus nerve, which then transmits signals via the nucleus tractus solitarius (NTS) to the satiety centre of the hypothalamus.
3) CCK-like peptides in the WP/WPH may bind to receptors present in the area postema adjacent to the NTS at the base of the fourth ventricle. The blood brain barrier overlying the fourth ventricle is leaky and could permit passage of a relatively small peptide like CCK.
4) CCK-like peptides in the WP/WPH may also bind directly to receptors on the afferent gastric vagus which could directly transmit the information to the NTS.

The Whey Protein and Whey Protein Hydrolysate

The terms "whey protein and/or whey protein hydrolysate which is/are capable of inducing the cellular release of glucagon-like-peptides and cholecystokinins", "WP" and "WPH" as used herein include all of the following; a single whey protein or whey protein hydrolysate which induces the cellular release of both the aforementioned satiety peptides and a mixture of two or more whey proteins or whey protein hydrolysates wherein the mixture induces the cellular release of both peptides even if at least one of the components induces the cellular release of only one of the peptides. References herein to WP and WPH are used to refer to both the singular and the plural use of whey protein and whey protein hydrolysate.

The WP may comprise any whey protein which is capable of inducing the cellular release of glucagon-like-peptides and cholecystokinins. The WPH may comprise any hydrolysed whey protein that is capable of inducing the cellular release of glucagon-like-peptides and cholecystokinins.

Suitable methods of hydrolysis of the whey protein include chemical processes (for example by acid hydrolysation) or enzymatical processes (including treatment with peptidases and bacterial or plant proteases) or by treatment with bacterial cultures. Examples of suitable enzymes which can be used to hydrolyse the WP include pepsin, trypsin and chymotrypsin.

It is especially preferred that the WPH comprises hydrolysates of β-lactoglobulin or α-lactalbumin, most preferably mixtures thereof. The weight ratio of the β-lactoglobulin or α-lactalbumin hydrolysates in the mixture is preferably in the range of from 5:1 to 1:5, more preferably 4:1 to 1:4, such as 3.5:1 to 1:2.

One particular WPH which may be used comprises from 5 to 20% by weight of aspartic acid, 10 to 25% by weight of leucine, 5 to 20% by weight of lysine and 10 to 32% by weight of glutamic acids.

The WPH may have a degree of hydrolysis in the range of up to 20%, preferably of from 1 to 15%, more preferably of from 2 to 10%, such as 5 to 9%. The degree of hydrolysis is determined by OPA methodology (Lee K S, Drescher D G., Fluorometric amino-acid analysis with o-phthaldialdehyde (OPA), Int. J. Biochem. 1978; 9(7): 457-467).

The WP and WPH preferably have a weight average molecular weight in the range of from about 1000 Dalton to 12000 Dalton, preferably of from 2000 Dalton to 8000 Dalton. It is preferred that 4 to 40% by weight, more preferably 10 to 30% of the WPH has a weight average molecular weight in the rage of from 2000 to 5000 Daltons and/or 1 to 30% by weight, more preferably 2 to 20% of the WPH has a weight average molecular weight in the range of from 5000 to 10000 Daltons.

The WP and WPH preferably have a pH in the range of from 6 to 9 at 20° C. in a 10 mg/ml solution in de-ionised water, more preferably of from 6.5 to 8.

WP and WPH according to the invention are known in the art and are commercially available. A description for one method to obtain the WPH is described in WO 01/85984 A1. A suitable commercially available source of the WPH is the Biozate™ range of whey protein hydrolysate products from Davisco Foods Inc, Minnesota, USA. The products designated "Biozate 1, 3 and 5" have been found to be especially suitable.

The WP and/or WPH is/are used in the preparation of edible compositions. The term "preparation" as used herein includes all suitable techniques of producing edible compositions, for example, mixing, blending, homogenising, high-pressure homogenising, emulsifying, dispersing, and/or encapsulating. The WP and/or WPH may be included in the edible composition by any suitable method known in the art and these methods will depend upon the type of edible composition.

The WP and/or WPH may be micro-filtered or ion-exchanged (either as the hydrolysate or as the parent protein). It may be enhanced with glutamine, alanine, cystine and branched chain amino acids.

Method of Administering the WP and/or WPH

The invention also provides the aforementioned methods for inducing satiety in a human or animal, for improving or controlling perception of body image, for controlling body weight, for controlling calorie intake and/or for helping adherence to a dietary plan, by administering an effective amount of the WP and/or WPH.

Furthermore the invention provides a method for altering the rate of gastric emptying, gastrointestinal (GI) transit and/or nutrient uptake from the GI cells of a human or animal, by administering to a human or animal an effective amount of the WP and/or WPH of the invention.

The total effective amount of WP and/or WPH administered according to the method may vary according to the needs of the person to whom it is administered. Typically total amounts of from 0.1 g to 150 g will be administered, preferably 1 g to 80 g, more preferably 5 g to 50 g per day. The effective daily amount may be administered by a single dose or by multiple doses.

The WP and/or WPH may be administered to the animal or human in any suitable form, for example as a capsule, tablet, solution, or, preferably as part of an edible composition as described herein including bar products and liquid products such as ready-to-drink products.

The Edible Composition

The edible composition may be in the form of a nutritional composition or supplement (such as a tablet, powder, capsule or liquid product), a food composition (product) such as a meal replacement product or a beverage.

A nutritional composition or supplement as used herein refers to a composition or supplement which provides at least one biologically beneficial agent such as vitamins, minerals, trace elements, the WPH etc and which is intended to supplement the amount of such agents obtained through normal dietary intake.

A food composition according to the invention may be any food which can be formulated to comprise the WP and/or WPH and which also contains at least one of protein, fat, and/or carbohydrate. It is preferred that the food composition is one intended to be used in a weight loss or weight control plan.

Such products typically have a controlled calorie content and are of a lower calorie content than the equivalent 'full calorie' food composition, for example, the so-called 'diet' or 'low calorie' products. Examples include "low-calorie" drinks and "low-calorie" snack products such as bars. It is also preferred that the food composition is a meal replacement product.

Suitable food compositions according to any aspect of the invention may be suitably selected from dairy based products (such as milk based products and drinks), soy based products, breads and cereal based products (including pasta and cereal bars), cakes, biscuits, spreads, oil-in-water emulsions (such as dressings and mayonnaise), ice creams, desserts, soups, powdered soup concentrates, sauces, powdered sauce concentrates, beverages, sport drinks, health bars, fruit juices, confectionery, snack foods, ready-to-eat meal products, pre-packed meal products, and dried meal products etc.

A meal replacement product as referred to herein refers to a product which is intended to replace one or more conventional meals per day; they are of a controlled calorie content and are generally eaten as a single product. Examples of meal replacement products include; liquid products such as milk or soya-based drinks, soluble powders used to prepare those drinks and drinks prepared therefrom, bars, soups, cereal or noodle or pasta-based products, desserts such as rice puddings, custards and the like. Meal replacement products are generally used by consumers following a calorie controlled diet.

Meal replacement products are especially preferred according to the present invention. They have been found to provide good satiety effects combined with restricted calorie content in a convenient form. It is especially preferred that the meal replacement product is a ready to drink liquid, a liquid produced from a soluble powdered product, a soup, a dessert, a bar, a cereal based or pasta based or noodle based product, or, a soluble or dispersible powdered product.

The edible composition may be for example; a solid product, a powdered product, a tablet, a capsule, a liquid, a flowable, spoonable, pourable or spreadable product or a bar etc. The edible composition may be a powder which is mixed with a liquid, such as water or milk, to produce a liquid or slurry product (such as a meal replacement product).

The edible compositions comprise a total amount of from 0.1% to 80% by weight of the WP and/or WPH based on the weight of the composition, preferably 0.1 to 40 or 50% wt, more preferably 0.5 or 1 to 30% wt, most preferably 2 or 5 to 20% wt. The edible compositions preferably comprise an amount of from 0.1 to 80% by weight, preferably 1 to 50%, of hydrolysates of β-lactoglobulin, α-lactalbumin or mixtures thereof based on the weight of the composition.

According to one embodiment of the invention, the edible compositions may comprise less than 20 g in total per serving, or per product where the product is used as a single serving, of the WP and/or WPH whether or not the above-mentioned amounts are used.

If the edible composition is a liquid or flowable composition, such as liquid meal replacement product or a soup, then the total amount of WP and/or WPH will preferably be in the range of from 0.1 to 40 or 50% by weight, more preferably 0.5 or 1 to 30% wt, most preferably 2 to 20% wt based on the total weight of the composition.

According to one aspect of the invention, the edible composition is a liquid or flowable composition which comprises protein, wherein the protein comprises 0.1 to 50% by weight based on the weight of the composition of WPH according to the invention and 50% or less of the total calories in the edible composition are provided by the total protein present in the composition (including the WPH). It is especially preferred that the composition comprises a total amount of from 0.5 to 30% by weight based on the weight of the composition of the WPH and 40% or less of the total calories in the edible composition are provided by the total protein present in the composition.

According to another aspect of the invention, the edible composition is a liquid or flowable composition comprising 0.1 to 80% by weight based on the weight of the composition of WPH of the invention and further comprising added vitamins and/or minerals selected from at least one of vitamins A, B1, B2, B3, B5, B6, B11, B12, biotin, C, D, E, H, K and calcium, magnesium, potassium, zinc and iron.

If the edible composition is a bar or other solid product product such as bar meal replacement product, then the amount of WP and/or WPH will typically be in the range of from 0.1 to 80% by weight, preferably 0.1 to 40% by weight based on the total weight of the composition. It is especially preferred that the bar compositions comprise β-lactoglobulin, α-lactalbumin, or hydrolysates thereof, or a mixture thereof in a total amount of from 0.1 to 80% by weight based on the weight of the composition. For the avoidance of doubt, such a composition does not include powdered or particulate compositions.

The edible composition will typically comprise protein in addition to the WP and/or WPH. The total amount of protein in the composition is preferably an amount of from 0.1 to 30 or 40% by weight of the edible composition. It is preferred that the compositions comprise 0.5 to 25% wt of total protein, preferably 1 to 20% wt. In the liquid or flowable compositions the protein present provides up to 50% of the total calories of the edible composition, more preferably between 20% and 50%, most preferably between 25% and 50%. For the other types of edible compositions, these amounts are preferred but are not essential.

The edible composition may comprise edible fats, preferably in an amount of up to 60 or 70% by weight based on the weight of the composition, more preferably from 0.5 to 30 or 35% wt, most preferably from 0.75 to 10 or 20% fat. Any suitable fat may be used with vegetable fats being especially preferred for example, vegetable fats, plant oils, nut oils, seed oils, or mixtures thereof. Saturated or unsaturated (monounsaturated and poly-unsaturated) fats may be used.

The edible compositions may also comprise one or more carbohydrates, preferably in an amount of from 1 to 95% by weight based on the weight of the composition, more preferably 5 to 70% wt, most preferably 10 to 60% wt, such as 15 to 50% wt.

Any suitable carbohydrate may be used, for example sucrose, lactose, glucose, fructose, corn syrup, maltodextrins, starch, modified starch or mixtures thereof.

The edible composition may also comprise dietary fibres, for example in an amount of from 0.1 to 40 or 50% by weight based on the weight of the composition, preferably 0.5 to 20% wt.

The edible composition may comprise dairy products such as milk, yoghurt, kefir, cheese or cream for example in an amount up to 70% by weight based on the weight of the composition, preferably 1 to 50% wt. Alternatively the edible composition may be soy-protein based, with the soy-protein used in the same amounts. The inclusion of these ingredients will be chosen so that the desired amount of protein, fat and carbohydrates etc are included in the edible composition.

The edible composition may comprise one or more emulsifiers. Any suitable emulsifier may be used, for example lecithins, egg yolk, egg-derived emulsifiers, diacetyl tartaric esters of mono, di or tri glycerides or mono, di, or triglycerides. The composition may comprise an amount of from 0.05 to 10% by weight, preferably from 0.5% to 5% wt, of the emulsifier based on the weight of the composition.

The edible composition may also comprise stabilisers. Any suitable stabiliser may be used, for example starches, modified starches, vegetable or microbial gums, pectins or gelatins. The composition may comprise an amount of from 0.01 to 10% by weight, preferably 1 to 5% wt of stabiliser based on the weight of the composition.

The edible composition may comprise up to 60% by weight of fruit or vegetables pieces or particles, concentrates, juice or puree based on the weight of the edible composition. Preferably the compositions comprise 0.1 to 40% wt, more preferably 1 to 20% wt of these ingredients. The amount of these ingredients will depend upon the type of edible composition; for example soups will typically comprise higher levels of vegetables than will a milk based meal replacement drink.

The edible composition may also comprise 0.1 to 15% by weight of edible salts based on the weight of the composition, preferably 3 to 8% wt. Any edible salts may be used, for example, sodium chloride, potassium chloride, alkali metal or alkaline earth metal salts of citric acid, lactic acid, benzoic acid, ascorbic acid, or, mixtures thereof. Calcium salts may also be used such as calcium chloride and calcium caseinate.

The edible composition may comprise one or more cholesterol lowering agents in conventional amounts. Any suitable, known, cholesterol lowering agent may be used, for example isoflavones, phytosterols, soy bean extracts, fish oil extracts, tea leaf extracts.

The edible composition may comprise up to 10 or 20% by weight, based on the weight of the composition, of minor ingredients selected from added vitamins, added minerals, herbs, spices, flavourings, aromas, antioxidants, colourants, preservatives or mixtures thereof. Preferably the compositions comprise of from 0.5 to 15% by weight, more preferably 2 to 10% of these ingredients. It is especially preferred that the compositions comprise added vitamins and minerals. These may be added by the use of vitamin premixes, mineral premixes and mixtures thereof. Alternatively the vitamins and/or minerals may be added individually. These added vitamins and/or minerals are preferably selected from at least one of vitamins A, B1, B2, B3, B5, B6, B12, biotin, C, D, E, H, K and calcium, magnesium, potassium, zinc and iron. Iodine, manganese, molybdenum, phosphorus, selenium and chromium may also be included.

The amounts of protein, fat, carbohydrate and other ingredients in the edible composition will vary according to the product format of the composition and also, where required, according to national or regional legislation.

If the edible composition is a meal replacement product then the calorie content of the product is preferably in the range of from 50 kilocalories (kcals) to 600 kcals, more preferably 100 kcals to 500 kcals, most preferably 150 or 200 kcals to 400 kcals per serving of the meal replacement product.

The compositions may be made by any suitable method known in the art; such methods are well known to those skilled in the art and do not need to be described further here.

The edible composition may be consumed by a human or an animal in connection with any one or more of the following; the treatment of obesity or being overweight; to improve or maintain the perception of body image; aiding compliance with a dietary plan e.g. to control, reduce or maintain body weight; to extend the time elapsed between meals; to control, maintain or reduce daily calorie intake; to suppress appetite.

The WP and/or WPH may be used in the preparation of an edible composition, which composition (after consumption by a human or an animal) induces a prolonged period for gastric emptying, or prolonged gastrointestinal (GI) transit or prolonged nutrient uptake from the GI cells compared to the consumption of a substantially nutritionally equivalent composition not comprising the WP and/or WPH.

A nutrient as referred to herein may be any component of a food product from which the consumer derives physiological benefit. Examples include macro-nutrients such as carbohydrates, fats and proteins or micro-nutrients such as vitamins, minerals, and trace elements. Fibres, although not absorbed by the body, are considered herein as nutrients. Water, although it provides a benefit to the body, is not considered as a nutrient.

The consumption of a composition comprising the WP and/or WPH according to the invention may occur as a part of a dietary plan, such as those intended to reduce or control body weight. For example, a subject following that plan may be better able to reduce, control or maintain their body weight, e.g. by following the dietary plan for a longer period of time and/or adhering more closely to the plan as they feel less temptation to snack or over-eat. The term "dietary plan" as used herein includes those for controlling body weight and those followed for medical reasons.

Another advantage of the present invention is that it provides methods and compositions to treat obesity or alter gastric transit and nutrient uptake in the body, which compositions can be simply eaten rather than needing to be injected as occurs with some hormones used in the treatment of obesity.

The invention is further described by way of the following examples which are to be understood as not limiting. Further examples within the scope of the invention will be apparent to the person skilled in the art.

EXAMPLES

Examples 1 and 2: Stimulated Release of GLP 1 and CCK in Cultured GLUTag Cells 1. Materials a) Whey Protein Hydrolysate:

The whey protein hydrolysate used was Biozate 1 which is a commercially available material from Davisco Foods International Inc., Le Sueur, Minn., U.S.A. Biozate 1 comprises a mixture of hydrolysed β-lactoglobulin and α-lactalbumin.

The technical specification of Biozate 1 is given below. The pH is 8.0. The degree of hydrolysis, as measured by the OPA method referred to hereunder, is 5.5+/−1.5. The molecular weight profile (Daltons) is: 30 to 45% greater than 10,000, 7 to 12% in the range 5000 to 10000, 15 to 25% in the range 2000 to 5000, 30-45% less than 2000 as measured by SEC-HPLC.

b) GLUTag Cells:

The GLUTag cells were obtained under licence from Toronto General Hospital, Toronto, Canada. GLUTag cells are an L cell line from intestinal endocrine tumors arising in the large bowel in proglucagon-simian virus 40 large T antigen transgenic mice. These cells are further described in the publication by Drucker D. J. et al (1994): Activation of proglucagon gene transcription by protein kinase A in a novel mouse enteroendocrine cell line. *Mol Endocrinol* 8:1646-1655.

c) Materials for Cell Culture:

Dulbecco's Modified Eagles Medium (DMEM) and bovine serum (FBS) were obtained from Invitrogen Ltd (Paisley, Scotland, UK).

2. Method

GLUTaq cells were grown during incubation at 37° C. in DMEM containing 10% (vol/vol) FBS. The medium was changed every 3 to 4 days until cell confluence was achieved. The cells were then trypsinized, plated in 24-well cultures plates ($0.5 \times 10^5$ cells/well) and the plates were stored under the same incubation conditions as described above. After 3 days storage the cells were washed twice with DMEM containing 0.5% (vol/vol) FBS and then, to four series (A to D) of 3 wells, different amounts of Biozate 1 were added as detailed below. Thus, each series was prepared in triplicate. A control sample which did not have any added Biozate 1 was also prepared in triplicate.

Series A—0.5 mg/ml Biozate 1
Series B—3 mg/ml Biozate 1
Series C—5 mg/ml Biozate 1
Series D—10 mg/ml Biozate 1

The plates were incubated as detailed above and after incubation for 1 hour an aliquot was taken from each plate to measure CCK release. A further aliquot was taken from each plate after 2 hours incubation to measure GLP-1 release. The aliquots were treated as detailed below before being tested to determine CCK or GLP-1 release.

The aliquots were collected and 50 μg/ml phenylmethanesulfonyl fluoride (PMSF) was added thereto. The aliquots were frozen at −80° C. for subsequent analysis for CCK and GLP-1 secretion. The aliquots were defrosted and centrifuged (5000 g) to remove cell debris. The CCK and GLP-l release from the GLUTaq cells was then tested.

CCK release was measured using a commercial enzyme immunoassay kit (from Phoenix Pharmaceuticals, Belmont, Calif., USA) which measures CCK 26-33 non-sulfated and sulfated. According to the test kit specifications, the intra-assay variation is <5% and the inter-assay variation is <14%.

GLP-1 release was measured using a commercial ELISA kit (from Linco Research Inc., St Charles, Mo., USA). This kit measures biologically active forms of GLP-1 [i.e. GLP-1 (7-36 amide) and GLP-1 (7-37)]. Prior to measuring GLP-1 release, the aliquots were diluted 1 parts to 10 parts with DMEM containing 0.5% (vol/vol) FBS to bring the GLP-1 concentration within the standard detection range of the ELISA kit.

FIG. 1 shows the concentration of GLP-1 secreted from GLUTaq cells into the media after 2 hours incubation at 37° C. with the Biozate 1.

FIG. 2 shows the concentration of CCK secreted from GLUTaq cells into the media after 1 hour incubation at 37° C. with Biozate 1.

On both FIGS. 1 and 2, the x axis shows the series and the concentration of Biozate 1 used. The y axes of FIGS. 1 and 2 show the concentration of GLP-1 or CCK secreted from GLUTaq cells into the media after incubation. For FIG. 1 the concentration is expressed in pico moles per liter (10 M) and for FIG. 2 in nanograms/ml.

Cell viability was positively determined using the CytoTox 96$^R$ non-radioactive cytotoxicity assay (Promega, Madison, USA) in order to prove that peptide release was not due to cell death.

From the results in FIGS. 1 and 2, it can be seen that the whey protein hydrolysate used (a mixture of β-lactoglobulin and α-lactalbumin hydrolysates) results in the release of both GLP-1 and CCK from the GLUTaq cells into the media.

Example 3

Meal Replacement Bar Product

A meal replacement bar product comprising WPH may be prepared according to the formulation below.

| Ingredient | Percentage by weight |
| --- | --- |
| Honey | 16.0 |
| Sucrose | 10.0 |
| Biozate 1 (WPH) | 13.0 |
| Whey protein*[1] | 13.0 |
| Chopped dried fruit and nuts | 10.0 |
| Soy flour | 5.0 |
| Peanut butter | 5.0 |
| Maltodextrin | 4.0 |
| Oats | 6.0 |
| Bran fibre | 2.0 |
| Flavourings | 2.0 |
| Vitamin/mineral premix | 2.0 |
| Chocolate flavoured coating | to 100% wt |

*[1]not according to the present invention.

The bar is made by thoroughly mixing together the honey and maltodextrin with the peanut butter. The remaining ingredients except the chocolate flavoured coating are added and the mixture is further mixed and formed into a bar shape. To coat it the bar is passed through a curtain of molten chocolate flavoured coating. The bar is allowed to cool to solidify the coating.

The edible composition shows good satiety effects compared to the equivalent composition wherein the whey protein hydrolysate is replaced by the same amount of cow's milk protein.

Example 4

Ready to Drink Liquid Meal Replacement Product

A meal replacement ready to drink liquid comprising WPH may be prepared according to the formulation below.

| Ingredient | Percentage by weight |
| --- | --- |
| Water | 75.5 |
| Sucrose | 2.0 |
| Biozate 1 (WPH) | 5.0 |
| Skimmed milk solids | 2.0 |
| High fructose corn syrup | 8.0 |
| Carageenan gum | 1.0 |
| Vegetable oil | 2.0 |
| Caramel flavouring | 1.5 |
| Colourings, other flavourings | 1.0 |
| Vitamin/mineral premix | 2.0 |

The ingredients were added to the water and the composition was mixed until an homogenous product was obtained.

The edible composition shows good satiety effects compared to the equivalent composition wherein the whey protein hydrolysate is replaced by the same amount of cow's milk protein.

Example 5

Ice Tea Product

An ice tea product (concentrate) comprising WPH may be prepared according to the formulation below. The tea may be made by mixing the ingredients together, with stirring, until a substantially homogenous product is obtained. The product may be cooled as desired.

| Ingredient | Percentage by weight |
| --- | --- |
| Maltodextrin | 39.4 |
| Tea powder | 9.0 |
| Aspartame | 2.5 |
| Peach flavour | 3.6 |
| N&A apricot flavour | 1.2 |
| Citric acid | 9.0 |
| Magnesium oxide | 0.2 |
| Biozate 1 | 10.0 |
| Vitamin premix | 0.3 |
| Calcium lactate | 23.2 |
| Water | to 100% wt |

The product shows good satiety effects (may be consumed as a diluted product) compared to the equivalent composition wherein the whey protein hydrolysate is replaced by the same amount of cow's milk protein.

In examples 3 to 5 the whey protein hydrolysate may be replaced by the non-hydrolysed whey protein according to the present invention.

The invention claimed is:

1. Method of treating and/or preventing obesity or being overweight in/of a human subject, said method comprising administering to the human subject an edible composition comprising an effective amount of whey protein hydrolysate, to induce the cellular release of glucagon-like-peptides and cholecystokinins, said whey protein hydrolysate having a molecular weight profile as measured by SEC-HPLC of 30 to 45% greater than 10,000 Dalton, 7 to 12% in the range 5000 to 10,000 Dalton, 15 to 25% in the range 2000 to 5000 Dalton and 30-45% less than 2000 Dalton.

2. The method according to claim 1, wherein the whey protein hydrolysate comprises hydrolysates of β-lactoglobulin, α-lactalbumin or a mixture thereof.

3. The method according to claim 2, wherein the hydrolysates of β-lactoglobulin and α-lactalbumin are present in the edible composition in a weight ratio of from 5:1 to 1:5.

4. The method according to claim 1, wherein the whey protein hydrolysate has a degree of hydrolysis in the range of from 1 to 20%.

5. The method according to claim 1, wherein the edible composition is a food composition used in a weight loss or weight control plan.

6. The method according to claim 1, wherein the edible composition comprises a meal replacement product.

7. The method according to claim 1, wherein the edible composition is selected from the group consisting of a ready-to-drink liquid, a liquid produced from a soluble powdered product, a soup, a dessert, a bar, a cereal based or pasta based or noodle based product, and a powdered product.

* * * * *